(12) United States Patent
Logan

(10) Patent No.: US 12,310,762 B2
(45) Date of Patent: May 27, 2025

(54) SMART WEARABLE DEVICE FOR TRACKING AND MONITORING INDIVIDUALS IN A CORRECTIONAL FACILITY

(71) Applicant: HLFIP HOLDING, LLC, Atlanta, GA (US)

(72) Inventor: Jonathan D. Logan, Tampa, FL (US)

(73) Assignee: HLFIP HOLDING, LLC, Atlanta, GA (US)

( * ) Notice: Subject to any disclaimer, the term of this patent is extended or adjusted under 35 U.S.C. 154(b) by 520 days.

(21) Appl. No.: 17/580,462

(22) Filed: Jan. 20, 2022

(65) Prior Publication Data

US 2022/0225947 A1 Jul. 21, 2022

Related U.S. Application Data

(60) Provisional application No. 63/139,778, filed on Jan. 20, 2021.

(51) Int. Cl.
*A61B 5/00* (2006.01)

(52) U.S. Cl.
CPC ............ *A61B 5/746* (2013.01); *A61B 5/0022* (2013.01); *A61B 5/681* (2013.01); *A61B 5/7405* (2013.01); *A61B 5/742* (2013.01); *A61B 5/7465* (2013.01)

(58) Field of Classification Search
CPC ....... G06F 1/163; A61B 5/746; A61B 5/0022; A61B 5/681; A61B 5/7405; A61B 5/742; A61B 5/7465; A61B 5/1113; A61B 2560/0209

USPC .............................. 320/112, 101; 361/679.03
See application file for complete search history.

(56) References Cited

U.S. PATENT DOCUMENTS

| | | | |
|---|---|---|---|
| 9,496,736 B1* | 11/2016 | Johansson | G06Q 10/00 |
| 9,659,477 B1* | 5/2017 | Obaidi | G08B 6/00 |
| 10,112,575 B2* | 10/2018 | Piccioni | H02J 50/80 |
| 10,762,764 B1* | 9/2020 | King | A61B 5/0077 |
| 11,537,835 B2* | 12/2022 | Turpin | G06K 19/0718 |
| 11,586,154 B2* | 2/2023 | Patnaikuni | G04G 17/08 |

* cited by examiner

*Primary Examiner* — M Baye Diao
(74) *Attorney, Agent, or Firm* — Outlier Patent Attorneys, PLLC

(57) ABSTRACT

The present invention relates to a smart wearable for use in correctional facilities. The correctional facility environment presents numerous challenges for which conventional smart wearables are not well suited, in particular maintaining sufficient battery power for operating the wearable over extended periods of time. The present invention provides a wearable with a removable battery pack which emphasizes improved battery life over conventional wearable aspects of small size and aesthetic appearance. The smart wearable disclosed herein is particularly well suited for correctional facilities due to the ability to power the wearable without the use of cables or wires for power or charging purposes. The smart wearable further provides for the ability to monitor inmate location and behavior which can be used to detect or predict undesirable actions.

14 Claims, 10 Drawing Sheets

SMART WEARABLE DEVICE FOR TRACKING AND MONITORING INDIVIDUALS IN A CORRECTIONAL FACILITY

CROSS-REFERENCE TO RELATED APPLICATIONS

This application claims the benefit of U.S. Provisional Application 63/139,778, filed Jan. 20, 2021, titled "SMART WEARABLE DEVICE FOR TRACKING AND MONITORING INDIVIDUALS IN A CORRECTIONAL FACILITY," which is herein incorporated by reference in its entirety.

BACKGROUND

In the field of smart wearable devices, there is a trend that devices are getting smaller and less bulky. Batteries that are placed in such devices are also tending to get smaller to accommodate smaller devices and to make them less bulky. This can cause such smart wearable devices to have very limited battery life. While aesthetics may be a driving force towards smaller, less bulky smart wearable devices for general public use, in a corrections environment functionality is of far greater importance than aesthetics. In particular, in a corrections environment, a wearable with increased battery life, power management approaches and an array of functional capabilities that can be accessed remotely and on demand as needed are substantially more important than size and appearance of a wearable.

In addition, smart wearable devices typically require some downtime, which is characterized as time when the device must be removed from the person of a wearer during recharge time. This downtime reduces the functionality of smart devices i.e. these devices are essentially useless during the time that they are removed from the user during recharge times. Indeed, regardless of the advances in battery technology, this issue prevents smart wearable devices from being deployed in critical situations where downtime is highly undesirable for tracking purposes. In the context of a correctional facility setting, frequent removal of a smart wearable for recharging purposes would result in inmates being untracked and unmonitored for extended periods of time leading to uncertainty regarding inmate location and activity which could present an opportunity for inappropriate behavior by inmates.

In addition, smart wearable devices require wires or cables as part of the charging process. Even in the case of wireless charging capabilities, the charger itself still includes a power cable being plugged into an outlet. This presents a problem for smart wearable devices for tracking and monitoring individuals in a correctional facility. Typically, inmates cannot have access to wires or cables because of a concern that such could be used for purposes of harm to self or others.

Furthermore, the trend towards smaller devices and smaller batteries with shorter battery life is not ideal for use in correctional facilities because of the additional level of attention and resources that would be required to constantly keep the smart wearables charged. The current state of smart wearables and their associated trends, when applied to a correctional facility, would mean increased attention, time and resources from correctional facility personnel to ensure that smart wearable devices remain sufficiently charged in order to provide reliable value to the correctional facility for inmate tracking and monitoring purposes.

There is a need for a smart wearable for use in correctional facilities that addresses the above issues of short battery life, frequent smart wearable removal and smart wearable recharging, and allows for inmate tracking, monitoring, and alerts correctional facility personnel as appropriate as to the status of a smart wearable as well as providing data obtained from the smart wearable to correctional facility personnel.

SUMMARY

The present invention overcomes the above limitations by creating a smart wearable that is better suited for correctional facilities. This is achieved by providing a smart wearable that can be configured to be non-removable by the wearer (and designed with a locking mechanism such that it may only be removed by facility personnel), employs a battery pack that is sized for longer life (that also can be configured as non-removable by the wearer) in order to keep the smart wearable sufficiently charged in a way which does not require cables or wires. In addition, the smart wearable is configured with hardware and/or software to provide the ability of obtaining data gathered from the smart wearable, such as physiological and location tracking data for example, to assist the facility with their management of inmates and related custodial duties. Among other benefits provided by the smart wearable disclosed herein, include the ability to track and monitor inmate activities, conversations and electronic communications in order to be able to investigate and prevent inappropriate or criminal behavior within the correctional facility.

BRIEF DESCRIPTION OF THE DRAWINGS

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION

Figure 1:
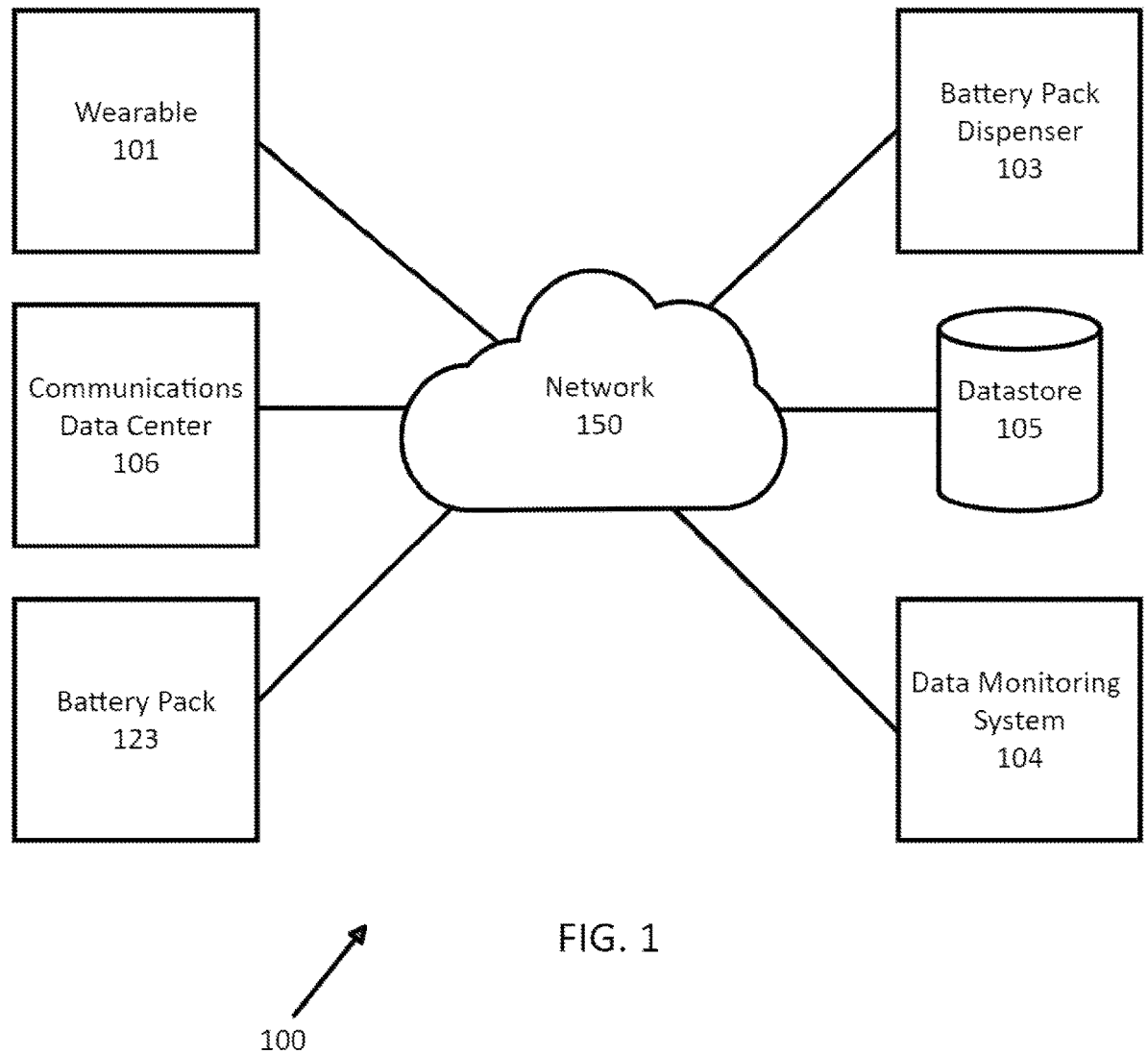
FIG. 1 illustrates a smart wearable and data monitoring system for use in a correctional facility in accordance with an exemplary embodiment of the invention.

One or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

FIG. 1 illustrates an exemplary embodiment of a smart wearable and data monitoring system for use in a correctional facility according to one embodiment. The system 100 includes a wearable 101, a battery pack 123 for the wearable, a battery pack dispenser 103, a data monitoring system 104, a communications data center 106, a datastore 105 and a network 150 over which the various systems communicate and interact. The various components of the system described herein work in concert to minimize "downtime" associated with the wearable 101 wherein the device is removed from the body of a person and/or otherwise limited during the recharge process. The various computing devices described herein are exemplary and for illustration purposes only. The system may be reorganized or consolidated, as understood by a person of ordinary skill in the art, to perform the same tasks on one or more other servers or computing devices without departing from the scope of the invention. In addition, the system 100 disclosed herein may be implemented with only a portion of the described components or with additional components as is appropriate for a given application.

The wearable 101, also referred to herein as a smart wearable or smart wearable device, is a device that may be attached to the portion of a body of a person. It may take the form of, for example, a watch, wrist band, bracelet, ankle bracelet, arm band, or may be a larger device spanning a larger portion of a wearer's limb. The wearable 101 may be a smart wearable device comprising a variety of components for acquiring data about the wearer and the surrounding environment. The wearable 101 may communicate with external components via a network as described further below. Some examples of components the wearable may comprise include a location tracking unit for tracking wearable location inside and outside a facility, a microphone for acquiring audio information of a wearer and their surroundings, a video camera for obtaining video information of a wearer and their surroundings, and a physiological data acquisition unit and/or sensors for obtaining physiological data of the wearer. An exemplary wearable which could be used in system 100 is discussed in more detail with respect to FIG. 2. In general, the wearable can acquire a variety of data which can be communicated via network 150 to be analyzed by the data monitoring system 104 and stored in a datastore 105 for later access and analysis.

Each wearable 101 may use a battery pack 123 for powering the wearable 101. The battery pack 123 refers to a removable battery pack that may be used to power the wearable 101. The battery pack 123 is distinct from an internal battery that is housed within the wearable 101, wherein the internal battery is not removable (or may be removed with certain tools). The battery pack 123 may power the wearable 101 and/or recharge an internal battery of the wearable 101. The battery pack 123 and/or the wearable 101 may communicate battery life information via network 150 to the other components of system 100 such as the data monitoring system 104, datastore 105 and battery pack dispenser 103. The battery pack 123 may be housed and/or charged in a battery pack dispenser 103. In one embodiment of the invention, battery packs 123 may be placed in the battery pack dispenser 103 for charging and/or may be retrieved from the battery pack dispenser 103 for use. In a corrections environment, where wearables can be used for tracking and monitoring of inmates to reduce the physical burden on facility personnel, maintaining battery power is essential to keeping the wearables powered on for tracking and monitoring purposes. If wearables lose power, then they lose their functionality which increases the burden on facility personnel to keep track of and monitor inmates as well as track down wearables and battery packs that need to be recharged. Therefore, it is important to monitor battery pack charge level so that appropriate measures can be taken to keep wearables powered on. For example, in one embodiment, a low battery signal may be communicated to the wearer and/or the battery pack dispenser 103 to indicate it is time to change the battery pack 123 and a charged battery pack should be provided via the battery pack dispenser 103 (or via other means). In one embodiment, a low battery signal may be communicated to the user and/or a data monitoring system 104 so that the system 100 can make appropriate notifications and arrangements for a replacement battery pack 123 to be provided to the wearer. For example, in the setting of a correctional facility, the data monitoring system may receive information regarding battery life of a battery pack and in turn notify correctional facility personnel so that a replacement battery is provided to the wearer before the associated wearable 101 completely runs out of battery.

The battery pack dispenser 103 may serve to provide charged battery packs 123 and/or receive depleted battery packs 123 for recharging. This may occur at a variety of different schedules/rules, including, but not limited to, regularly occurring battery exchange at approximately the same time every day so that a given wearable 101 is able to maintain suitable battery life. The battery pack dispenser 103 may involve a form of automated exchange such that a wearer of a wearable visits the battery pack dispenser 103, may be prompted for a form of identification and is then provided with a new charged battery pack 123 in exchange for a used battery pack. The identification may include an inmate identifier. In one embodiment, the wearable 101 may be programmed with the inmate identifier and automatically provide this identification information to the battery pack dispenser 103 when in proximity to the battery pack dispenser 103. The battery pack dispenser 103 may associate the inmate identifier with the returned battery pack and the newly dispensed battery pack 103 for tracking purposes. In one embodiment, the battery pack dispenser 103 may rely on facility personnel to assist the exchange of battery packs, such as in situations where a battery pack 123 includes a form of locking mechanism so that it cannot be removed by the wearer of the wearable. In these situations, facility personnel could assist the wearer with accessing the battery pack dispenser 103 in order to perform battery pack exchange. The battery pack dispenser 103 may comprise charging capabilities such that in the event no battery packs are available for exchange, a user may charge the battery pack for their wearable at the battery pack dispenser 103. The battery pack dispenser charging capabilities may serve to recharge returned batteries and/or keep batteries for distribution at or near full charge for exchange as needed.

The data monitoring system 104 may receive information from the wearable 101, battery pack 123, battery pack dispenser 103, and/or datastore 105 and process the received information to determine various characteristics of the wearer of a given wearable as well as identify patterns or trends associated with one or more wearables 101 and the associated wearer. The data monitoring system 104 may also output processed information to the datastore 105 for later review and analysis. In one embodiment, the data monitoring system 104 monitors battery charge information in an effort to keep wearables above a battery power threshold necessary to maintain certain functionality. In one embodiment, the data monitoring system 104 monitors information from battery pack dispenser 103 in addition to battery charge information from wearable 101 and/or battery pack 123 as a measure of compliance of the wearer with maintaining battery life at appropriate levels which may be established by the facility. The data monitoring system 104 may store or record information obtained from a wearable in association with an inmate identifier so that subsequent processing of wearable information can be associated with a corresponding user (i.e. inmate).

In one embodiment, the data monitoring system 104 uses location tracking information to track the locations of a given wearable so that it can be determined where a given wearable and the associated inmate are located at a given time. In addition, the data monitoring system may store this location information in a datastore 105 so that patterns of behavior based on location can be monitored over time. As one example, such monitoring may be used for purposes of contact tracing in case of an infectious disease or for investigating inappropriate or potentially criminal activity by monitoring which wearers tend to congregate with one another. The data monitoring system 104 may also use received information to automate certain manual tasks at facilities such as performing physical head counts. Instead of a physical head count, or as a supplement to physical head counts, the data monitoring system 104 may use received geolocation data to verify all inmates are appropriately accounted for. This may involve use of location tracking information and/or physiological information received from a wearable 101. For example, the data monitoring system 104 may use physiological data such as heart rate to ensure the wearable 101 is actively present on an individual and may additionally use location tracking information to ensure that an individual is located in their designated cell thereby providing assistance in performing inmate head counts. These are just a few examples of how the data monitoring system 104 can use various information to assess inmates within a correctional facility and the data monitoring system 104 could be used to process other obtainable information as would be apparent to one of ordinary skill in the art.

The communications data center 106 processes communication sent to and/or from an inmate. In one embodiment, the communications data center 106 may process communication to identify/filter communications that contain contraband and/or prohibited communications. Examples of contraband and/or prohibited data may include, but is not limited to, pornography, drugs, weapons, gang symbols, messages regarding or inciting a prohibited activity, etc. A variety of different mechanisms may be employed to identify/filter contraband and/or prohibited content, as would be readily apparent to a person of ordinary skill in the art, without departing from the scope of the invention, including, but not limited to: scanning postal mail (which automatically eliminates physical contraband such as drugs or weapons), searching for keywords within a communication, enabling manual review by staff, searching for images within the messages/communications, etc. In one embodiment, the communications data center 106 may process communication at the corrections facility. In another embodiment, the communications data center 106 may be remote from the corrections facility and may make permissible data available to the corrections facility. A variety of different mechanisms may be used to deliver the permissible communications data to the corrections facility and/or inmates at the correction facility. For example, the permissible communication may be printed and/or delivered to the inmate. In one embodiment, the permissible communication may be electronically communicated by sending the communication to an inbox that is associated with the inmate, by, for example, an inmate identifier. In one embodiment, the electronically delivered communication may be accessed by the inmate from a kiosk, a tablet, or a wearable 101. In one embodiment, the wearable 101 may be used to signal that the inmate is ready to receive communication from the communications data center 106. In one embodiment, the wearable 101 may be used to print a communication that the wearer may have received. In yet another embodiment, the wearable 101 may be used to track when a communication has been received and/or read by the recipient inmate, and to send a signal ultimately sent to communications data center 106, for example, reflecting the received and/or read status of the communication so that the sender of the communication may be able to receive a notification or status update accordingly. In one embodiment, the read receipt and/or receipt that a communication is obtained may be sent to any of the subcomponents described in FIG. 1 via a communication system described below in reference to FIG. 1.

The communications data center 106 may be a remote or cloud based data center. The communications data center 106 may comprise a server or network of computer servers and a database management system(s) for storing and providing remote access to communications to and from inmates in a correctional facility. The communications data center 106 may communicate with a wearable 101 associated with each inmate in order to transmit communications to and from the wearable associated with each inmate.

Network cloud 150 generally represents a network or collection of networks (such as the Internet or a corporate intranet, or a combination of both) over which the various components illustrated in FIG. 1 (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 150 or a combination of two or more such networks 150. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various systems and databases described herein.

The network 150 connects the various systems and computing devices described or referenced herein. In particular embodiments, network 150 is an intranet, an extranet, a virtual private network (VPN), a secure private network, a local area network (LAN), a wireless LAN (WLAN), a wide area network (WAN), a metropolitan area network (MAN), a portion of the Internet, or another network 421 or a combination of two or more such networks 150. The present disclosure contemplates any suitable network 150.

One or more links couple one or more systems, engines or devices to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable links coupling one or more systems, engines or devices to the network 150.

In particular embodiments, each system or engine may be a unitary server or may be a distributed server spanning multiple computers or multiple datacenters. Systems, engines, or modules may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to client/user devices or other devices in response to HTTP or other requests from client devices or other devices. A mail server is generally capable of providing electronic mail services to various client devices or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiments, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1, but would be readily apparent to a person of ordinary skill in the art. For example, the system may include databases for storing data, storing features, storing outcomes (training sets), and storing models. Other databases and systems may be added or subtracted, as would be readily understood by a person of ordinary skill in the art, without departing from the scope of the invention.

Figure 2A:
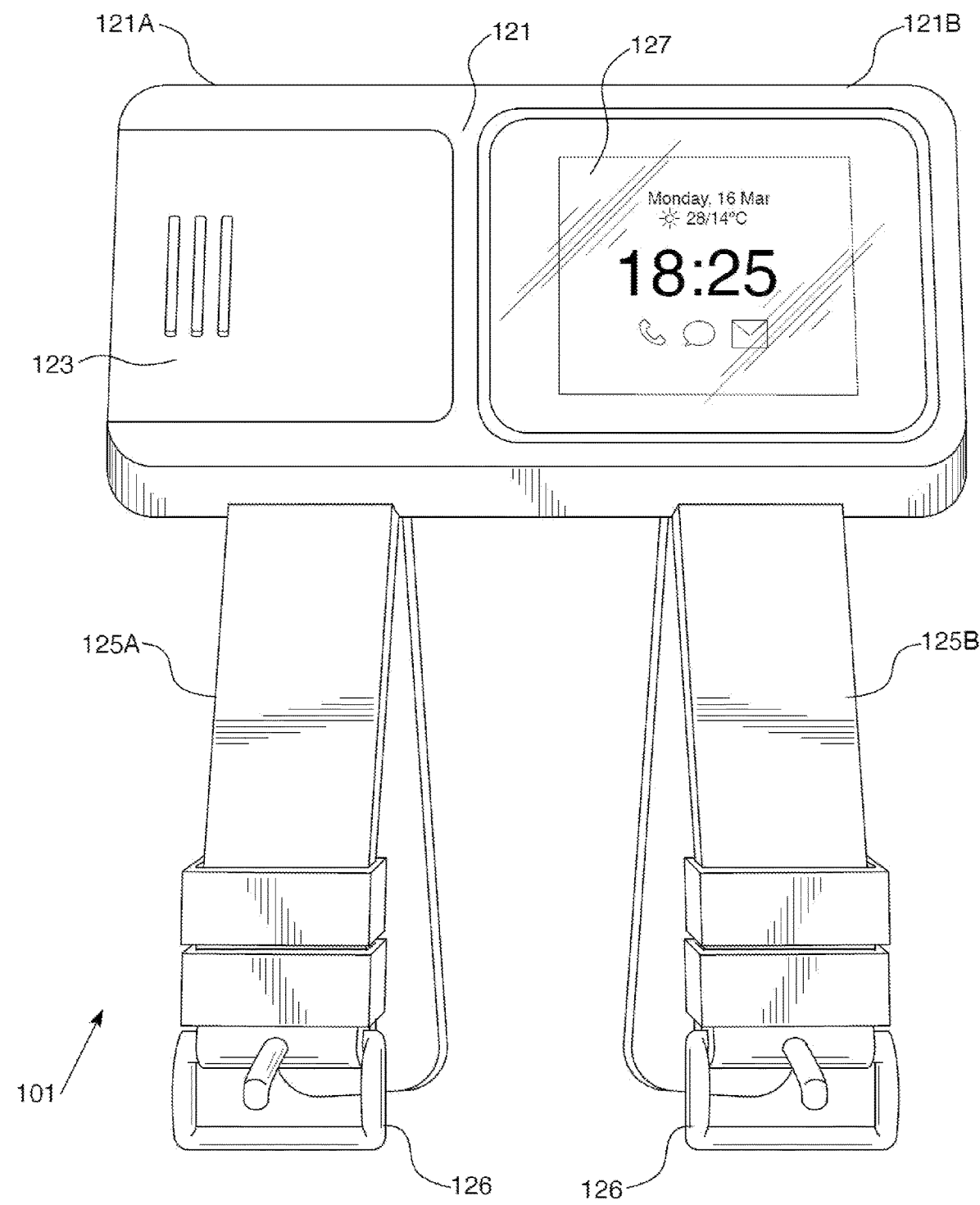
FIG. 2A illustrates a smart wearable device for use in a correctional facility and in conjunction with a data monitoring system in accordance with an exemplary embodiment of the present invention.
Figure 2B:
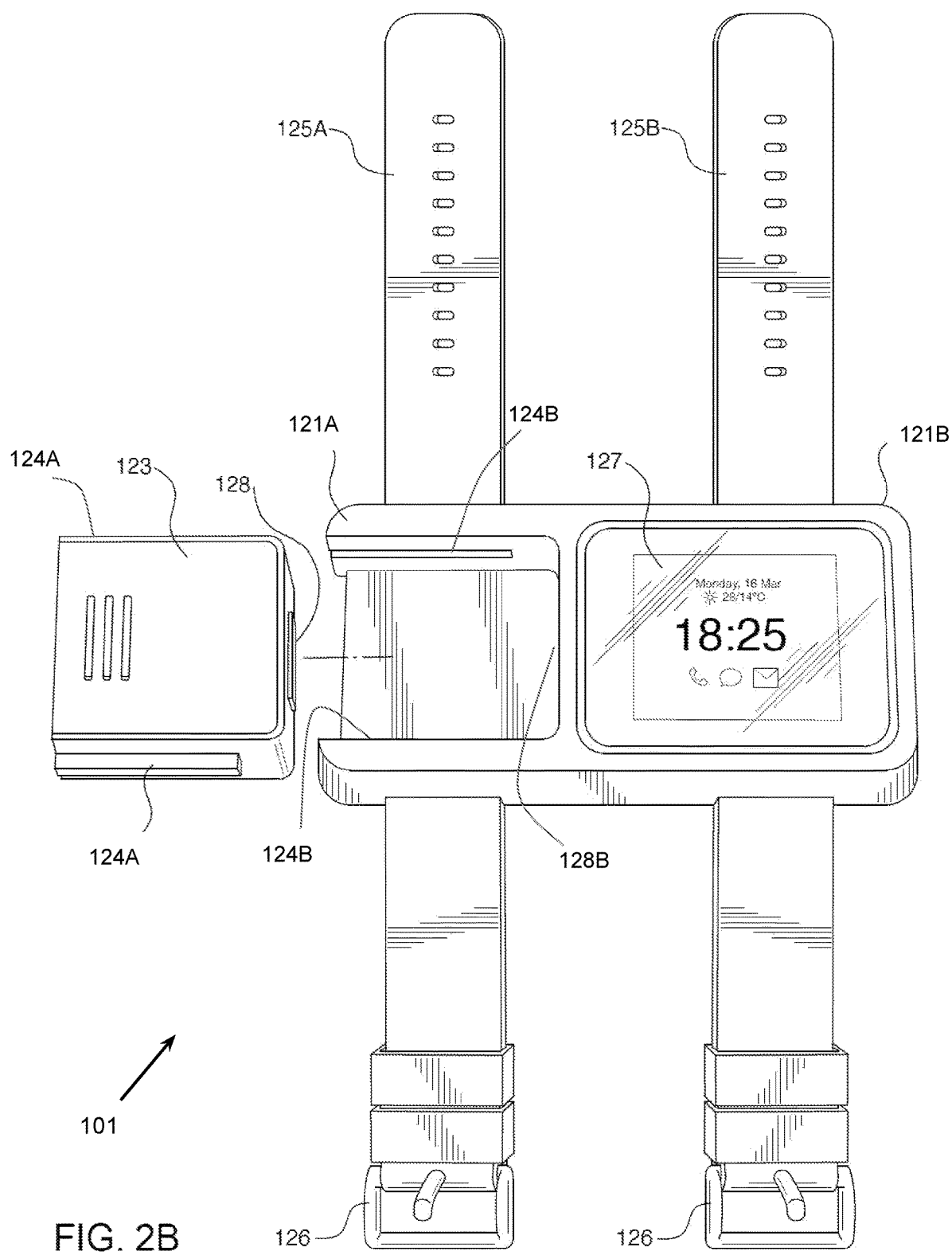
FIG. 2B illustrates a smart wearable device for use in a correctional facility and in conjunction with a data monitoring system in accordance with an exemplary embodiment of the present invention.

FIGS. 2A-2B illustrate an exemplary embodiment of a wearable 101 for use in a correctional facility. More specifically, the two figures illustrate an embodiment of the wearable 101 in two different configurations; FIG. 2A illustrates a wearable 101 wherein a removable battery pack 123 is attached to the wearable 101, and FIG. 2B illustrates a wearable 101 wherein a removable battery pack 123 is removed from the wearable 101. The wearable 101 comprises a housing 121, a removable battery pack 123, securing mechanisms 125A, 125B, 126, and a display 127. The housing comprises a first portion 121B and a second portion 121A. The wearable 101 comprises a battery securing mechanism 124A, 124B. The housing 121 comprises a battery pack interface 128B for engaging with a connection interface 128 of battery pack 123.

The housing 121 encloses and protects internal electronic components of the wearable 101 and interfaces with battery pack 123 to allow for electrical energy transfer from the battery pack to power the wearable 101. The housing 121 may comprise a first housing portion 121B comprising a display 127 and internal electronic components and/or control circuitry such as at least one processor and memory for executing various functions associated with the wearable. The housing 121 may comprise a second housing portion 121A comprising an interface to receive and engage with a removable battery pack 123. The housing 121 may comprise at least one recess or groove 124B for engaging with a corresponding protrusion 124A of the battery pack 123. Alternatively, the housing 121 may comprise at least one protrusion for engaging with at least one corresponding recess or groove of the battery pack 123. The housing 121 may comprise a battery pack interface 128B configured to engage with a corresponding interface of the battery pack 123. The battery pack interface 128B may allow for electrical energy transfer from the battery pack 123 to power the wearable 101, such as the electrical components of housing portion 121B. The housing 121 may be made of a durable material that is not easily damaged. The housing 121 may be at least one of waterproof, shockproof and tamperproof. These characteristics may be present with or without the battery pack attached.

The battery pack 123 provides electrical energy to power the wearable and/or charge the internal battery. It comprises an outer housing and at least one internal electrical energy storage element. The battery pack 123 may comprise a rechargeable internal electrical storage element(s). As illustrated in FIG. 2B, the battery pack may comprise at least one protrusion 124A which engages with a corresponding recess or groove 124B of the first portion of the housing 121A such that the battery pack is guided into position for interfacing with the housing 121 and to aid in securing the battery pack to prevent unintended detachment (e.g. preventing the battery pack from falling out of the housing 121). The battery pack 123 may comprise a protrusion 124A on multiple sides or faces of the battery pack. Alternatively, the battery pack may comprise at least one recess or groove for receiving a corresponding protrusion where the protrusion(s) are located on the housing 121 and serve to guide and secure the battery pack 123 in place within the housing 121. Battery pack 123 may engage with housing 121 in a locking configuration. In one embodiment, removal of the battery pack 123 from housing 121 may require use of a key or disengaging the battery from the locked configuration.

The battery pack may comprise a connection interface 128 configured to engage with a corresponding interface 128B of housing 121 and form an electrical coupling with housing 121 in order to provide electrical energy for use by internal components of housing 121. The electrical coupling may be via a direct electrical connection with housing 121. The electrical coupling may comprise magnetic contacts. The battery pack may comprise reverse polarization protection to prevent sparks or damage to battery pack and/or wearable. The electrical coupling may be through wireless or inductive power transfer without direct electrical interface. The battery pack 123 and/or connection interface 128 may comprise at least one magnet for engaging with a corresponding ferromagnetic material of housing 121 in order to pull and hold the battery pack 123 in secure engagement with housing 121. The magnet may comprise a permanent magnet or electromagnet. Alternatively, the housing may comprise at least one magnet which may be a permanent magnet or electromagnet and the battery pack may comprise the corresponding ferromagnetic material. Alternatively, both the housing 121 and battery pack 123 may comprise at least one magnet arranged such that opposite poles would face each other when the battery pack is properly inserted such that the magnet of the housing and the magnet of the battery pack exert an attractive force on one another to pull and secure the battery pack 123 in place in the housing 121. The magnet(s) may be and/or comprise an electric coupling.

The wearable may comprise securing mechanisms configured to secure the wearable to an individual or a portion thereof. In one non-limiting embodiment, the securing mechanism may be comprised of a first strap 125A, and/or a second strap 125B, and/or one or more buckles 126. A variety of other securing mechanisms may be used, as would be apparent to a person of ordinary skill in the art, without departing from the scope of invention, including, but not limited to, a stretchable loop (which may include a first stretchable loop and/or a second stretchable loop), etc. In one embodiment, the first strap 125A and second strap 125B may be integral with housing 121 or may be removably coupled to housing 121. In one embodiment, the first strap 125A may be coupled with a first portion of the housing 121A and the second strap 125B may be coupled with a second portion of the housing 121B. In another embodiment, the first strap 125A may be coupled with a second portion of the housing 121B and the second strap 125B may be coupled with a first portion of the housing 121A. Each strap 125A, 125B may comprise a buckle 126 which in combination with holes in straps 125A and 125B provide the ability to adjust the tightness of fit of straps 125A and 125B. In other embodiments, other mechanisms other than buckles may be used to secure the straps, as would be apparent to a person of ordinary skill in the art, without departing from the scope of the invention, including, but not limited to, velcro. Alternatively, in lieu of buckle 126, straps 125A and 125B may each be a unitary piece of material (e.g. a loop, ring, band) coupled with housing 121 and made of an elastic material that stretches to fit around a wearer's extremity (e.g. hand, foot) and then contracts in size or length in order to secure the wearable to a user's body part (e.g. forearm/wrist, lower leg/ankle). As an alternative to the first and second straps, a single strap, a cuff, a sleeve or the like may be used to secure the wearable to a body part of an individual as would be apparent to one of ordinary skill in the art. In addition, as an alternative to a buckle 126, the wearable 101 may be designed to be non-removable by the wearer. For example, the wearable may include an alternate form of securing mechanism such as a locking mechanism that must be unlocked (e.g. via a key or lock releasing mechanism) in order to be removed so that inmates of a correctional facility are unable to remove the wearable. Such may be accomplished by replacing buckle 126 with an alternative locking mechanism for securing at least one strap to an individual. Securing mechanisms 125A, 125B, 126 may comprise at least one of durable material that is not easily damaged, tamper proof material that is not easily torn, cut or otherwise degraded, and waterproof material.

The display 127 may comprise any suitable display screen for displaying information. The display 127 may comprise a touchscreen. The display may be used to display various information and media as is discussed in more detail below with respect to FIG. 2C.

Figure 2C:
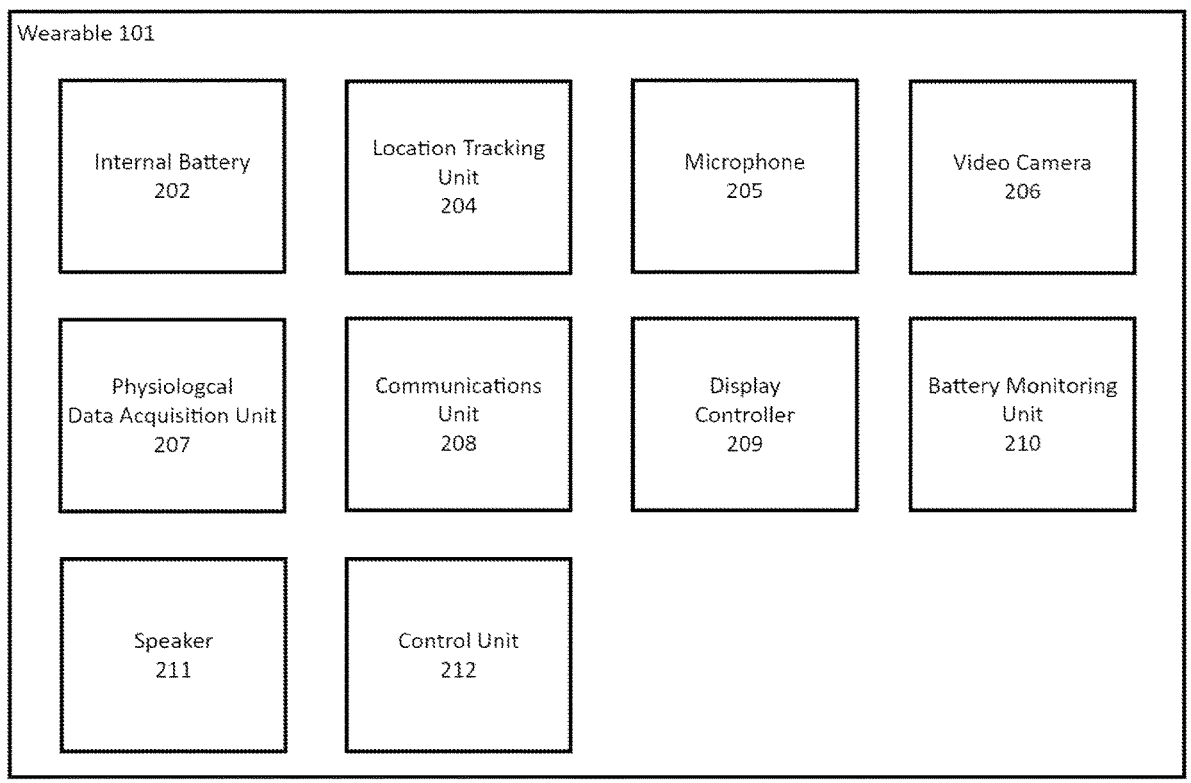
FIG. 2C illustrates a smart wearable device for use in a correctional facility and in conjunction with a data monitoring system in accordance with an exemplary embodiment of the present invention.

FIG. 2C illustrates an exemplary embodiment of the electronic components of a wearable 101 which could be used in combination with a data monitoring system in a facility such as a correctional facility according to one embodiment. The exemplary wearable 101 comprises an internal battery 202, a location tracking unit 204, a microphone 205, a video camera 206, a speaker 211, a physiological data acquisition unit 207, a communications unit 208, a display controller 209, a battery monitoring unit 210, and a control unit 212. Other systems and units may be used, as would be readily understood by a person of ordinary skill in the art, without departing from the scope of the invention. The wearable 101 disclosed herein may be designed with only a portion of the described components or with additional components as is appropriate for a given application as would be recognized by one of ordinary skill in the art.

The internal battery 202 may be a rechargeable battery with sufficient capacity to power the wearable 101 for an extended period of time under normal operating conditions. The internal battery may be charged via wired or wireless charging technologies. The internal battery 202 may serve as a backup power supply when a battery pack 123 is not connected to the wearable 101 or when the battery pack 123 is too low to power the wearable 101. In one embodiment, the internal battery 202 may also be recharged by a removable battery pack 123 when the battery pack 123 is connected to the wearable 101. The wearable 101 may be configured such that limited functionality is allowed without a battery pack 123 or when at least one of the internal battery 202 and battery pack 123 approach low levels. This may serve to preserve critical or essential functions of the wearable 101 by preserving battery life of the internal battery 202 until a replacement battery pack is attached or until battery recharging can be achieved.

The location tracking unit 204 serves to track the location of a wearable 101 both inside and outside a facility. A variety of different location technologies may be used to track the location of a wearable 101, as would be understood by a person of ordinary skill in the art, without departing from the scope of the invention. The location tracking unit 204 may be a computing system associated with the facility. The location tracking unit 204 may interface with a facility based tracking system to determine a location of a wearable, and hence the wearer within the facility. The location tracking unit 204 may also include global position system technology and/or cellular service based tracking capabilities in order to track the location of the wearable inside and outside the facility. This may provide the benefit of determining the location of an individual should they end up outside a facility without authorization, such as an escaped inmate. In one embodiment, location may be determined based on a computation. For example, a computation may determine the distance between a wearable and at least one component, such as a nearby router or access point, via position data associated with the location tracking unit 204.

The microphone 205 may be used for sensing audio in the area around the wearer. In one embodiment, the microphone may be used for audio conversations between the wearer and other inmates, facility personnel or outside personnel when communication is authorized. The microphone 205 may be used to sense and transmit audio from the wearer or the surrounding environment and sensing and transmitting may be triggered or controlled by the wearable 101 or an external device such as a data monitoring system. Recordings or live audio from the microphone 205 may be transmitted from the wearable for facility personnel or others to listen to. Recordings or live audio from the microphone 205 may be transmitted from the wearable to a data monitoring system for analysis of the audio such as reviewing the audio transmission for keywords for determining any discussions of criminal activity or requests for help. Recording or live audio from the microphone 205 may be sent to a datastore for later analysis by facility personnel or investigators. Microphone 205 may obtain audio from a user such as the user using the microphone for dictation purposes wherein the obtained audio may be processed in combination with communications unit 208 for sending messages via approved communication channels (e.g. after screening, etc.) as discussed below.

The video camera 206 may be used for sensing video data in the area around the wearable. In one embodiment, the video camera 206 may be used for video conferencing between the wearer and facility personnel or individuals outside the facility, such as for a remote video visitation session, when communication is authorized. The video camera 206 may be used to record and transmit video from the wearer or the surrounding environment and recording and transmitting may be triggered or controlled by the wearable 101 or an external device such as a data monitoring system. Recordings or live video from the video camera 206 may be transmitted from the wearable for facility personnel or others to view. Recordings or live video from the video camera 206 may be transmitted from the wearable to a data monitoring system for analysis of the video such as reviewing the video transmission for inappropriate or criminal activity or requests for help. Recording or live video from the video camera 206 may be sent to a datastore for later analysis by facility personnel or investigators.

The speaker 211 may output audible sounds in accordance with input received from other units or components of the wearable 101. For example, speaker 211 may output alerts or alarms associated with low battery levels or the need for battery pack replacement and/or recharging in accordance with battery monitoring unit 210 as discussed below. Speaker 211 may output audio in accordance with communications unit 208 as discussed below. For example, speaker 211 may output audio from pre-recorded video or audio messages, live video or audio calls, text to speech audio associated with postal mail and or email, etc. The speaker 211 may output entertainment media such as music, sound corresponding to video being watched (e.g. movie, episodes, live stream event, etc.), audio books, news information, etc. Any suitable speaker may be used for outputting audible sounds as would be apparent to one of ordinary skill in the art.

The physiological data acquisition unit 207 may be used to capture physiological data of the wearer. The physiological data acquisition unit 207 communicates with various monitors or sensors for recording physiological data such as a temperature sensor, an optical sensor, an electrocardiography sensor, a heart rate monitor, blood pressure monitor, blood oxygenation monitor, a movement or activity monitor, and a sleep monitor among other types of sensors and monitors for measuring physiological data as would be recognized by one of ordinary skill in the art. Any of these sensors may be integrated into the wearable. Any of these sensors may be independent of the wearable and configured to couple with and/or communicate with the wearable to provide sensor data to the physiological data acquisition unit 207 of the wearable 101.

The communications unit 208 enables the wearable 101 to access data from or provide data to a messaging system such as email, jail mail, text messages, etc. via a network interface. The communications unit 208 may provide the ability for the wearer to receive and send a variety of communications such as text messages, pre-recorded video or audio messages, email, transcribed mail or messages, scanned postal mail and the like. Use of the communications unit 208 may be controlled under a set of facility specific protocols to ensure appropriateness of incoming and outgoing communications. For example, in a correctional facility, the wearer may have limited access to the communications unit 208 and any transmission to/from the communications unit 208 may follow correctional facility review for contraband and inappropriate content. The communications unit 208 may process audio data obtained from the microphone and convert to text for processing by a screening tool prior to allowing the audio data to be transmitted to an identified destination. Communications unit 208 may provide a user with access to digital communications to which the user is authorized to view. For example, communications unit 208 may access a database of digitized postal mail communications, emails and the like which have been processed and screened for contraband prior to being accessible by the user via the wearable. The communications unit 208 may interface with a communications data center, such as communications data center 106 as described above, in order to provide the wearer with access to approved communications. Each wearable 101 may be associated with an inmate identifier so that communications unit 208 may authorize access to communications associated with the inmate associated with each wearable 101. Communications unit 208 may assign an inmate identifier to outgoing communications originating from a wearable 101 so that communications can be associated with a corresponding inmate for appropriate recording in a communications database such as that associated with communications data center 106 as described above.

Battery monitoring unit 210 monitors battery status information in order to evaluate battery charge levels. Battery monitoring unit 210 may determine if and when a battery pack should be replaced or recharged. Battery monitoring unit 210 obtains battery status information associated with at least one of an attached rechargeable battery pack 123 and internal battery 202. Battery monitoring unit 210 may interface with at least one of battery pack 123 and internal battery for obtaining battery status information. Battery monitoring unit 210 may obtain battery charge level information, for at least one of internal battery 202 and an attached battery pack, at threshold time intervals in order to check battery status and monitor changes in battery charge level over time. Battery monitoring unit 210 may generate timestamps and corresponding battery charge level information and provide this information for storage in a database for later analysis or monitoring of battery performance over time. Battery monitoring unit 210 may generate an alert when the charge level for at least one of an attached battery pack and an internal battery 202 falls below a threshold value. The alert may comprise at least one of a visual alert and audible alert which may be conveyed via speaker 211. The alert may comprise providing an electronic signal or notification to an external system which may coordinate battery replacement and/or recharging. Battery monitoring unit 210 may generate an indication or signal that the primary power source should be changed based on obtained battery charge level information. For example, battery monitoring unit 210 may provide an indication or recommendation to switch from the battery pack 123 as the main power source to the internal battery when battery charge level information associated with the battery pack 123 indicates the available electrical energy is below a threshold value. For example, battery monitoring unit 210 may provide an indication when an attached battery pack 123 falls below 20%, below 10%, or below 5% of the battery pack's maximum charge capacity. Battery monitoring unit 210 may compute an estimated usage time remaining based on the obtained battery status information. Battery monitoring unit 210 may obtain an electronic signal or notification from an external system indicating at least one of the need for battery pack replacement, a time for battery pack replacement, and a location for battery pack replacement. Battery monitoring unit 210 may provide this information or convert this information into a suitable format for display controller 209 in order to display battery pack replacement information on the wearable 101.

Display controller 209 may obtain information from at least one of an internal wearable component(s) and an external component(s) and cause a display, such as display 127, to display information in accordance with the obtained information. Display controller 209 may cause a display to show general information such as date, time, weather and the like under normal operating conditions. Display controller 209 may cause a display to show indicators or notifications when new communication information is available such as based on information obtained from communications unit 208. For example, display controller 209 may cause a display to provide an indication that a new screened message or postal mail communication has been processed and is available for viewing by the user of the wearable. Display controller 209 may cause a display to show screened messages or postal mail communications upon input resulting from interaction between a user and the wearable indicating the desire to view new or past communications which have been deemed appropriate for user viewing. Display controller 209 may cause the display of visual indicators or notifications associated with information obtained from battery monitoring unit 210. For example, notifications associated with at least one of battery life falling below various thresholds and upcoming battery pack replacement information such as date, time and location for battery pack exchange may be generated for display on a display of the wearable device. Display controller 209 may cause a display to display media content which a user is authorized to view such as digital books or magazines, movies or tv shows, live stream events, news clips or streams, etc.

Control unit 212 comprises a processor and memory configured to execute functions of the wearable 101 based on input received from at least one of internal components of the wearable 101 and external components or systems. Control unit 212 may obtain, from battery monitoring unit 210, an indication that an attached battery pack is below a threshold value and, in response, switch the main power supply source from an attached battery pack to the internal battery of the wearable device. Control unit 212 may obtain from battery monitoring unit 210, an indication that an attached battery pack is below a threshold value and, in response, disable certain functions and/or certain internal components or units of the wearable in order to prolong battery life and maintain certain functionality of the wearable 101. Control unit 212 may obtain an indication that an attached battery pack has become disconnected or that no battery pack is attached and, in response, disable certain functions and/or certain internal components or units of the wearable in order to prolong battery life of the internal battery and maintain certain functionality of the wearable 101. Control unit 212 may obtain, from communications unit 208, an indication associated with initiating a video call and, in response, activate microphone 205, speaker 211, video camera 206, and instruct display controller 209 to display incoming or received video content associated with the video call on display 127. Control unit 212 may send and/or receive signals to and from external systems such as data monitoring system 104 as described below. For example, control unit 212 may obtain, from an external system, an indication to gather information associated with headcount analysis and, in response, activate at least one of location tracking unit 204 and physiological data acquisition unit 207 and provide corresponding information such as wearable geolocation data and/or physiological sensor data to external system for headcount analysis. Control unit 212 may send and/or receive other signals or information associated with other functional aspects of data monitoring system 104 as discussed below.

Figure 2D:
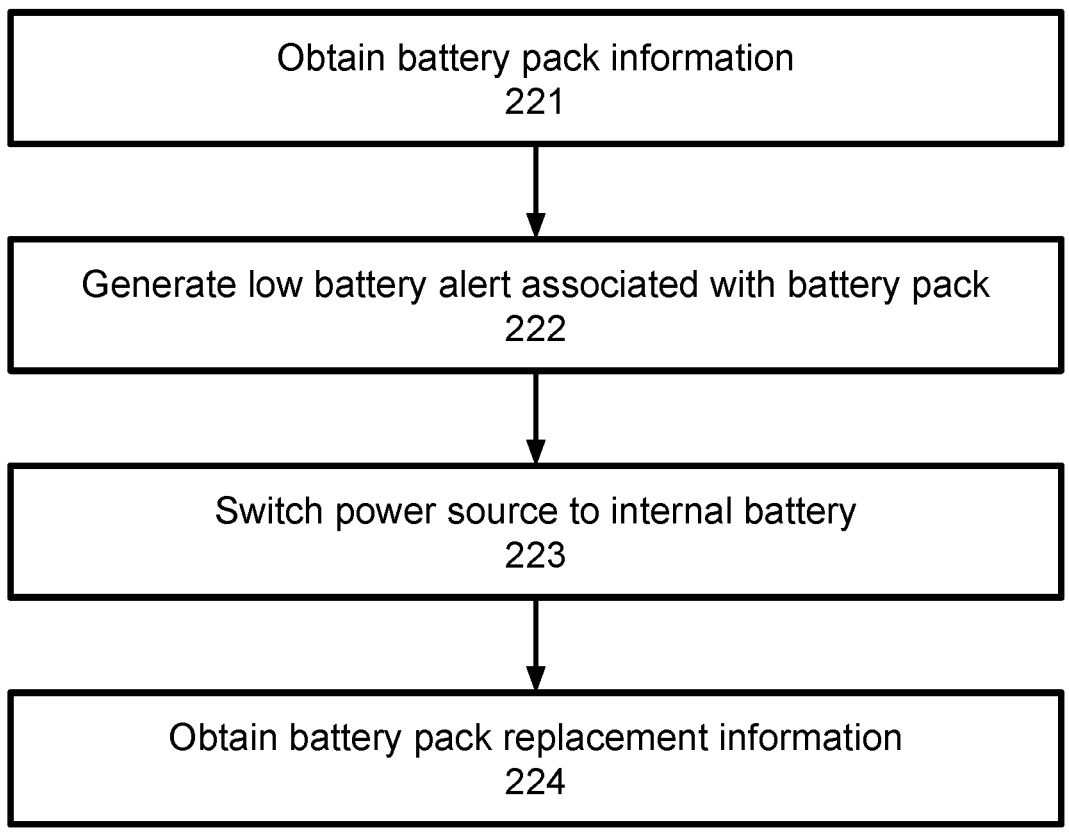
FIG. 2D illustrates, in accordance with an embodiment of the invention, a process for managing power on an exemplary device with an internal battery and an attachable external battery.

FIG. 2D illustrates an exemplary embodiment of a process for managing battery power for a smart wearable device to ensure the smart wearable device can remain powered on. The process comprises obtaining battery pack information 221, generating a low battery alert associated with the battery pack 222, switching the power source of the wearable to an internal battery 223, and obtaining battery pack replacement information 224.

At step 221, the process comprises obtaining battery pack information which may comprise at least one of battery pack charge level, estimated battery pack usage time remaining, a battery pack identifier, and battery pack location.

At step 222, a low battery alert may be generated by a wearable when the obtained battery pack information indicates that remaining battery life is below a threshold value as discussed above. The alert may comprise at least one of a visual alert, an audible alert and an electronic signal or notification to an external system. Generating a low battery alert may comprise analyzing the obtained battery pack information to determine if at least one of the charge level and the estimated battery pack usage time remaining are below a threshold value. The threshold value may be a value indicative of the need to replace the battery pack. For example, the threshold value may be 20%, 10%, or 5%. Alternatively, the threshold value may be based on estimated usage time remaining such as 5 hours remaining, 2 hours remaining, or 1 hour remaining. These threshold values are merely exemplary and threshold values could be adapted as necessary to indicate the need for an upcoming battery pack replacement to keep the smart wearable powered as would be apparent to one of ordinary skill in the art. For example, the threshold values may vary based on a correctional facility schedule. During morning or daytime hours the thresholds may be lower since a battery pack replacement may be more feasible. However, as evening approaches, the threshold values may be higher so that a battery pack replacement may be completed prior to a period of scheduled sleep for inmates of the correctional facility so that the wearable devices can remain powered on through the period of scheduled sleep. In these scenarios exemplary threshold values comprise 8 hours, 10 hours, or 12 hours remaining.

At step 223, the wearable may switch from using the battery pack as a primary power source for powering the wearable to an internal battery of the wearable as the primary power source. In one embodiment, the wearable may continue to operate with normal functionality while using the internal battery as the primary power source. In one embodiment, the wearable may be configured to have limited functionality while using the internal battery as the primary power source. Upon battery pack replacement or recharge, the wearable may switch from the internal battery to the battery pack as the primary power source. Switching to a battery pack as the primary power source may comprise restoring full functionality of the wearable if functionality was limited due to the lack of an attached or sufficiently charged battery pack.

At step 224, the wearable may obtain battery pack replacement information. The battery pack replacement information may comprise at least one of a battery pack replacement timeframe and a battery pack replacement location. The battery pack replacement information may be obtained from an external system which monitors a plurality of battery packs and coordinates battery pack replacement planning and notification. The battery pack replacement information may comprise a battery pack dispenser location where a replacement battery pack is available or will be available at the battery pack replacement timeframe.

Figure 3:
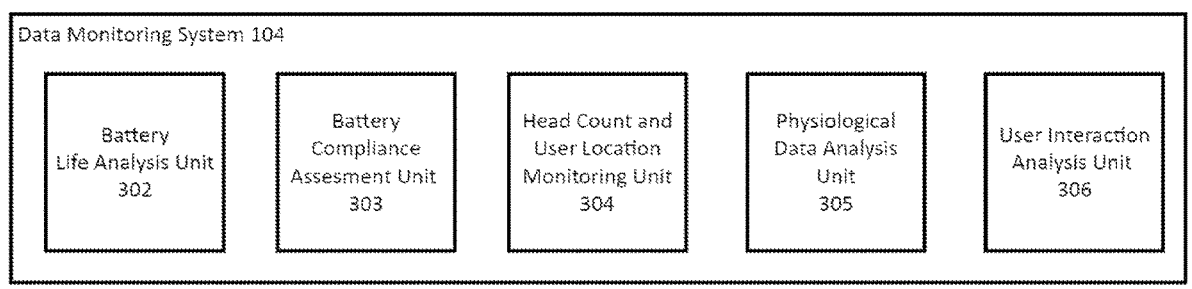
FIG. 3 illustrates a data monitoring system for use in a correctional facility in accordance with an exemplary embodiment of the present invention.

FIG. 3 illustrates an exemplary data monitoring system 104 for processing information received from a smart wearable device, in accordance with one embodiment of the invention. The data monitoring system 104 includes a battery life analysis unit 302, a compliance assessment unit 303, a head count and user location monitoring unit 304, a physiological data analysis unit 305, and a user interaction analysis unit 306. Other systems and units may be used, as would be readily understood by a person of ordinary skill in the art, without departing from the scope of the invention. In addition, the data monitoring system 104 disclosed herein may be implemented with only a portion of the described components or with additional components as is appropriate for a given application.

The battery life analysis unit 302 serves to track battery life status of wearables and battery packs associated with a given facility. The battery life analysis unit 302 may receive periodic status updates from a wearable and/or a battery pack regarding current charge capacity. The battery life analysis unit 302 may also receive alerts when a particular wearable and/or battery pack has reached a predetermined threshold. For example, in one embodiment this threshold may indicate the battery is critically low and should be replaced immediately. In one embodiment, the threshold may be a function of time of day such that a battery can be recharged or replaced prior to the wearer going to sleep so that sufficient battery power is provided through the duration of the wearer's sleep and the battery need not be replaced in the middle of their sleep cycle. The battery life analysis unit 302 may also analyze internal batteries of wearables and battery packs over time to determine diminishing full battery capacity as the batteries age in order to determine when older batteries should be replaced and taken out of rotation for recycling and new replacement batteries ordered and put into rotation.

The battery compliance assessment unit 303 may receive information from a wearable, battery packs, battery life analysis unit 302 and/or a battery pack dispenser and process this information to determine if a wearer is compliant with keeping their wearable and/or battery pack sufficiently charged. The compliance assessment unit 303 may determine whether a user is complying with facility specific protocols for battery life and acquiring replacement battery packs when necessary or if the wearer shows trends of repeated non-compliance. For example, if the facility has a protocol in place for regular periodic battery pack changes, such as daily at a set time or twice a day such as morning and evening, the compliance assessment unit 303 may use information from a wearable, battery packs, battery life analysis unit 302 and/or a battery pack dispenser to determine if a wearer is regularly following the established protocol for changing battery packs. In one embodiment, a protocol may require the wearer bringing the wearable to designated charging stations (such as battery pack dispenser 103 or a separate charging station) and the compliance assessment unit 303 may include determining patterns of behavior associated with the wearer regularly charging their wearable at a charging station.

The head count and user location monitoring unit 304 may receive information from one or more wearables within a facility and perform automated head counts and ensuring inmates of the facility are present and in appropriate locations at designated times. For example, the head count and user location monitoring unit 304 may rely on physiological data to ensure that a wearable is active and on an occupant such as by verifying a valid heart rate or other physiological parameter associated with each wearable. In addition, the head count and user location monitoring unit 304 may use location tracking information from a wearable in order to determine that occupants of the facility are in appropriate locations. For example, if a facility has a curfew and designated sleep time, the head count and user location monitoring unit 304 may verify that all occupants are in their designated room, cell, etc. as is appropriate for a given facility.

The physiological data analysis unit 305 may analyze a variety of physiological data received from a wearable to determine different health related characteristics of a wearer. In one embodiment, the physiological data analysis unit 305 analyzes temperature data of the wearer to determine the presence of a fever which may serve as an indication of an underlying illness. In one embodiment, the physiological data analysis unit 305 may analyze movement or activity information, ECG information, and/or heart rate information in order to assess a wearer's exercise activity. The physiological data analysis unit 305 may also analyze ECG information and/or heart rate activity to identify cardiovascular issues such as atrial fibrillation or cardiac arrest and alert appropriate facility personnel if a medical emergency is identified. The physiological data analysis unit 305 may analyze sleep related information in order to determine sleep patterns and irregularities and identify sleep issues based on this information. In one embodiment, the physiological data analysis unit 305 may perform group analysis to analyze how a given wearer is performing compared to a larger group of individuals. This group analysis may allow for the identification of which occupants of a facility are underperforming/overperforming relative to the majority of occupants and provide an indication to facility personnel so that appropriate interventional measures can be taken to address individuals with lower than ideal health related statistics.

The user interaction and analysis unit 306 analyzes information received from one or more smart wearables to determine how wearers of wearables within a facility interact. The user interaction and analysis unit 306 may receive and analyze information from a wearable associated with location tracking, audio information from a microphone and/or video information from a video camera to assess how wearers are interacting. The user interaction and analysis unit 306 may monitor which occupants are communicating with one another based on proximity to each other as well as listen to conversations to hear what occupants are discussing and use such to intercept plans for inappropriate or criminal activity. The user interaction and analysis unit 306 may also rely on video to identify occupants of a facility who are attempting to communicate silently (without invoking any audio recording of the wearable) as an added measure to prevent inappropriate or criminal activity. Such information may be used to notify facility personnel of a need to investigate a particular individual or group of individuals. In addition, the user interaction and analysis unit 306 may perform such analysis in real-time and/or use historical data to identify patterns of behavior amongst facility occupants so that further investigation can be conducted as needed.

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments). Any of the above mentioned systems, units, modules, engines, controllers, components or the like may be and/or comprise computing hardware and/or software as described herein. For example, the wearable 101 and/or data monitoring system 104 and their subcomponents may be and/or comprise computing hardware and/or software as described herein in association with FIGS. 4-7.

Figure 4:
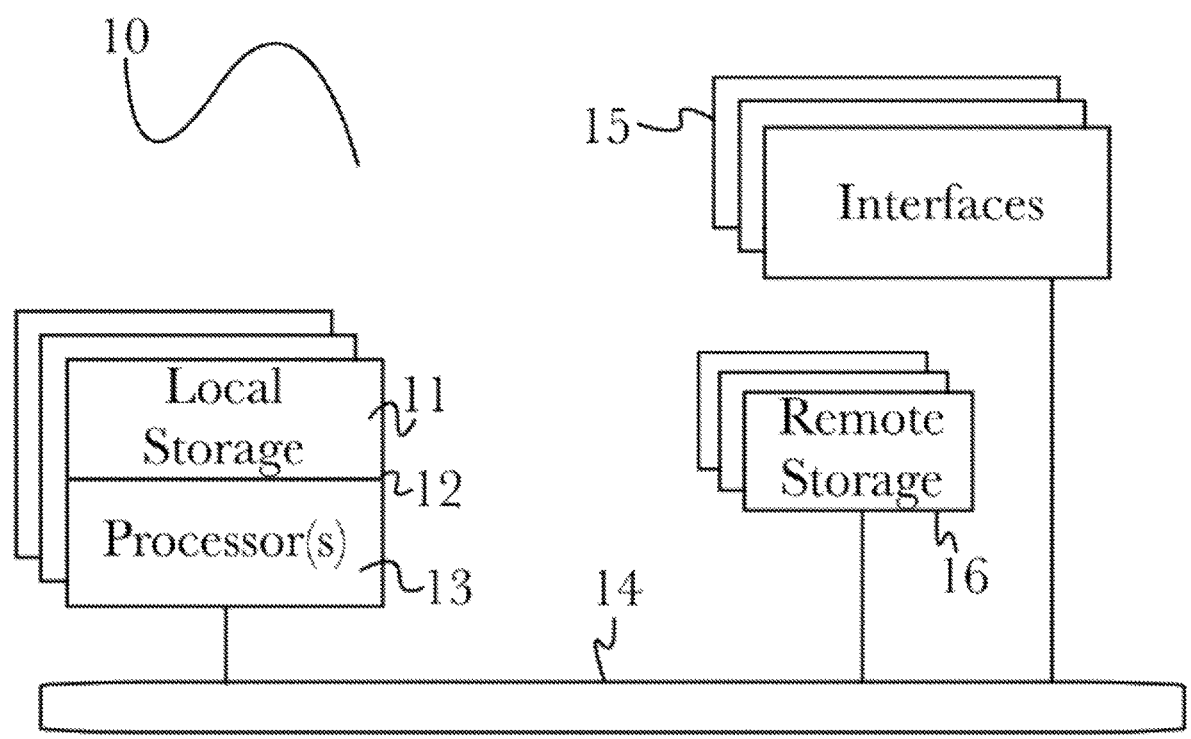
FIG. 4 illustrates one embodiment of the computing architecture that supports an embodiment of the inventive disclosure.

Referring now to FIG. 4, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 4 illustrates one specific architecture for a computing device 10 for implementing one or more of the embodiments described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, single processor 13 handles communications as well as routing computations, while in other embodiments a separate dedicated communications processor may be provided. In various embodiments, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 5:
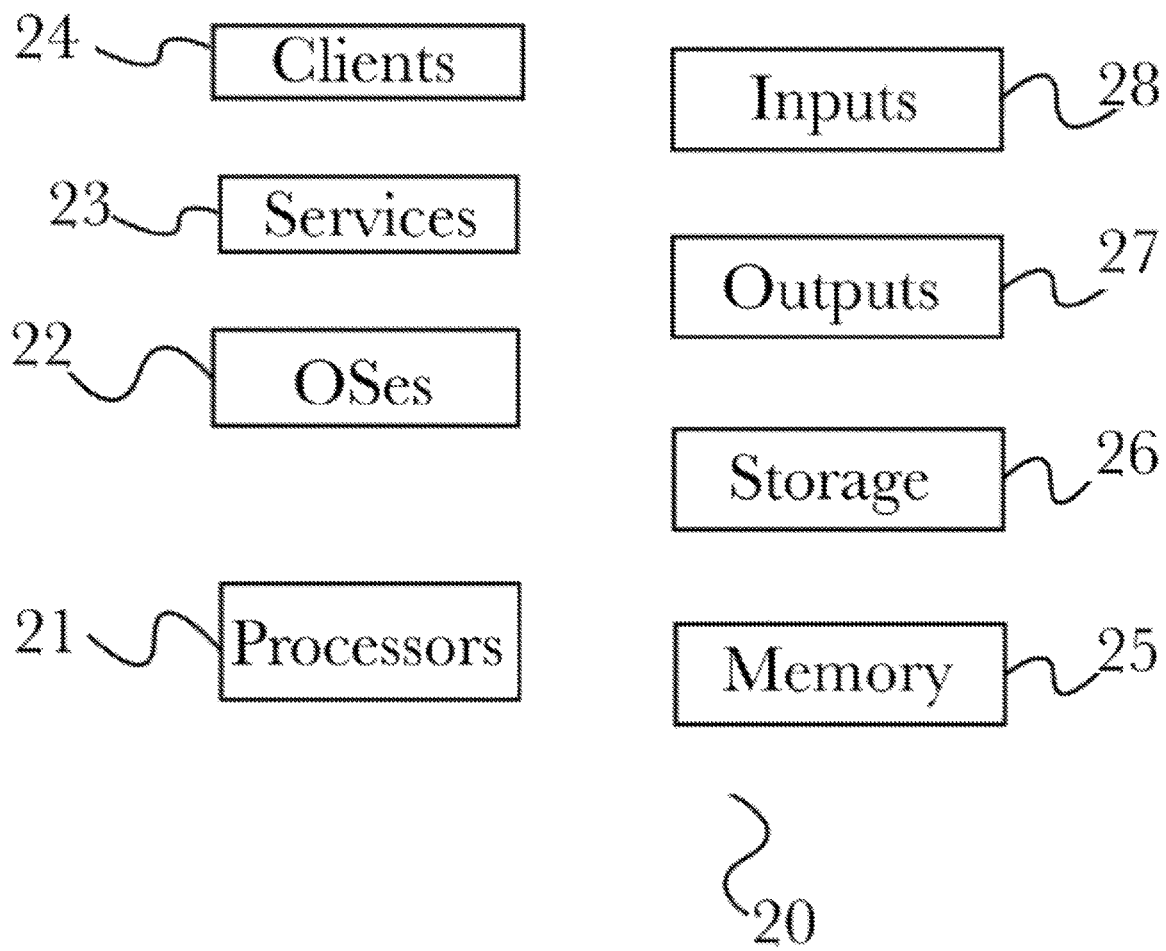
FIG. 5 illustrates components of a system architecture that supports an embodiment of the inventive disclosure.

In some embodiments, systems may be implemented on a standalone computing system. Referring now to FIG. 5, there is shown a block diagram depicting a typical exemplary architecture of one or more embodiments or components thereof on a standalone computing system. Computing device 20 includes processors 21 that may run software that carry out one or more functions or applications of embodiments, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 4). Examples of storage devices 26 include flash memory, magnetic hard drive, CD-ROM, and/or the like.

Figure 6:
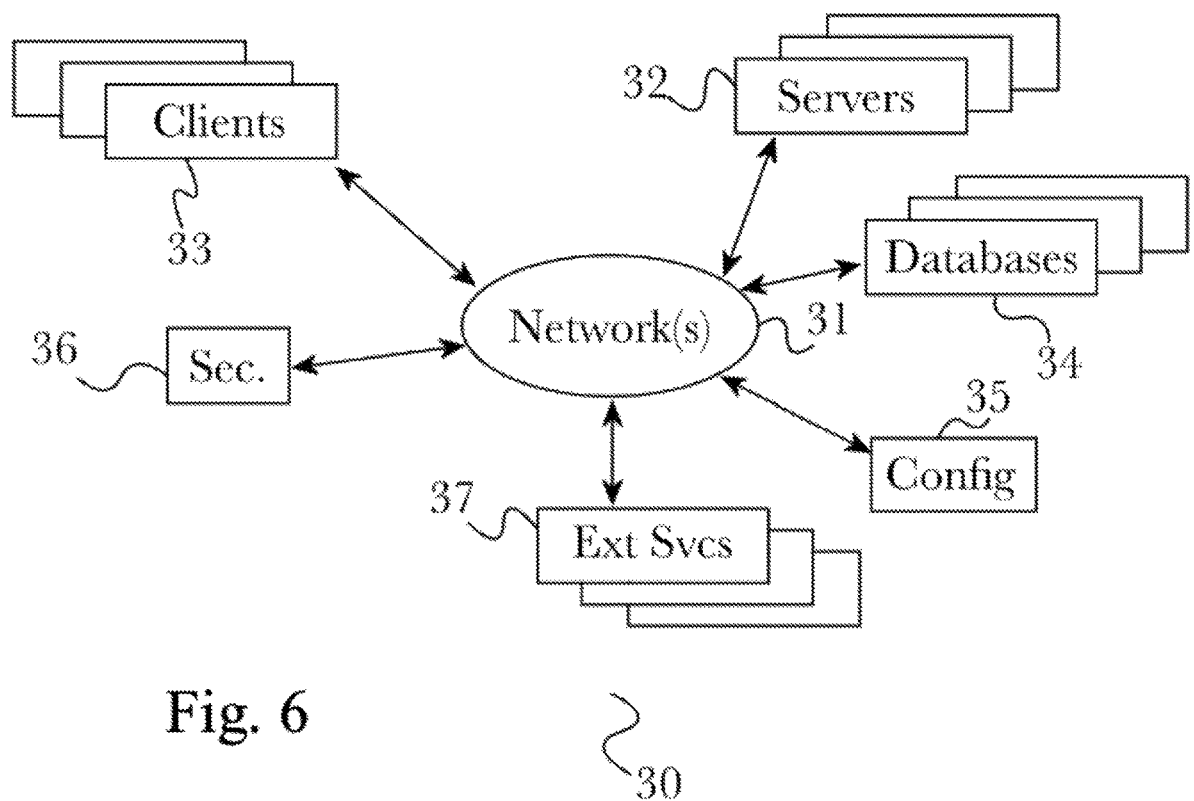
FIG. 6 illustrates components of a computing architecture that supports an embodiment of the inventive disclosure.

In some embodiments, systems may be implemented on a distributed computing network, such as one having any number of clients and/or servers. Referring now to FIG. 6, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 5. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some embodiments, clients 33 or servers 32 (or both) may make use of one or more specialized services or appliances that may be deployed locally or remotely across one or more networks 31. For example, one or more databases 34 may be used or referred to by one or more embodiments. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some embodiments may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments without limitation, unless a specific security 36 or configuration system 35 or approach is specifically required by the description of any specific aspect.

Figure 7:
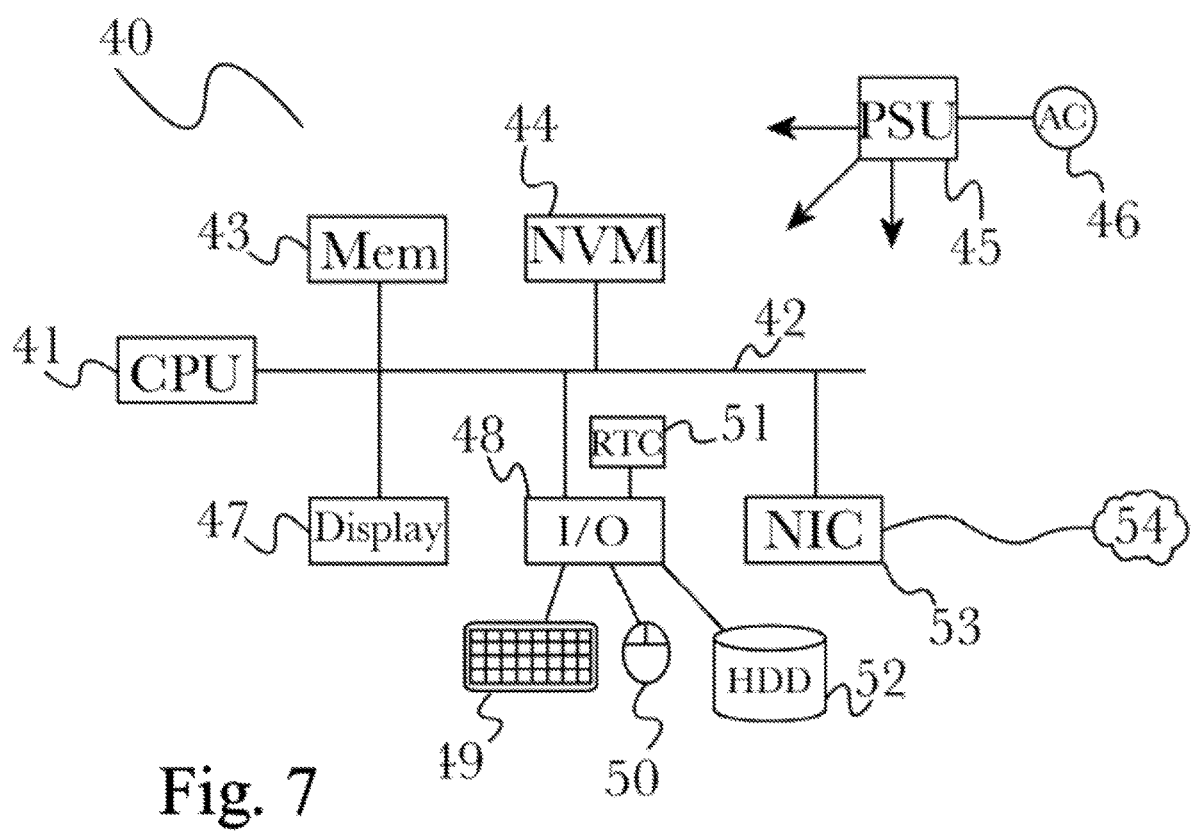
FIG. 7 illustrates components of a computing device that supports an embodiment of the inventive disclosure.

FIG. 7 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of various embodiments may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various embodiments described above. Accordingly, the present invention is defined by the claims and their equivalents. Although described herein with particular reference to a correctional facility the inventive aspects disclosed herein may be applied to wearable devices for use in other facilities or applications where extended battery life is important.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A smart wearable device for use by occupants of a correctional facility, the smart wearable device comprising:
   a removable battery pack;
   a first housing portion comprising:
      an internal battery installed inside the first housing;
      a display; and
      a processor;
   a second housing portion comprising:
      a battery pack interface configured to engage with a corresponding interface of the removable battery pack, the battery pack interface enabling the battery pack to power at least a portion of electrical components in the first housing portion; and
      a battery pack securing mechanism configured to secure the battery pack to the second housing portion;
   a securing mechanism coupled with at least one of the first housing portion and second housing portion, the securing mechanism configured to secure the first and second housing portions to an individual.

2. The smart wearable of claim 1, the battery pack securing mechanism comprising a recess in the second housing portion that engages with a protrusion on the removable battery pack.

3. The smart wearable of claim 1, wherein the removable battery pack comprises a magnetic contact that interfaces with a corresponding contact of the battery pack interface.

4. The smart wearable of claim 1, wherein the processor is configured to obtain battery pack status information at periodic time intervals and compute estimated battery pack usage time remaining.

5. The smart wearable of claim 1, wherein the processor is configured to cause at least one component of the first housing portion to use electrical energy from the internal battery when a charge level of the battery pack falls below a threshold value.

6. The smart wearable of claim 1, wherein the processor is configured to generate an alert when a charge level associated with the battery pack falls below a threshold value.

7. The smart wearable of claim 1, wherein the alert comprises at least one of a visual and audible alert.

8. The smart wearable of claim 1, wherein the alert comprises a signal transmitted to at least one external system.

9. The smart wearable of claim 1, wherein the processor is configured to obtain information associated with a planned battery pack exchange and cause the display to show corresponding battery pack exchange information.

10. The smart wearable of claim 8, wherein the information associated with a planned battery pack exchange comprises at least one of a location of a battery pack dispenser and a timeframe for completing the battery pack exchange.

11. The smart wearable of claim 1, the first housing portion further comprising a microphone.

12. The smart wearable of claim 1, the first housing portion further comprising a video camera.

13. The smart wearable of claim 1, the first housing portion further comprising a communication interface for receiving screened communications comprising at least one of digitized postal mail, email, and text message communications.

14. The smart wearable of claim 1, wherein the securing mechanism comprises a first strap and a second strap.

* * * * *